United States Patent [19]
Wright et al.

[11] Patent Number: 5,981,289
[45] Date of Patent: Nov. 9, 1999

[54] HYDROGEN SULFIDE ANALYZER

[75] Inventors: Paul G. Wright, Garland; David J. Shannon, Lincoln; Lowell R. Nickolaus, Lincoln; Randy J. Forman, Lincoln; Clifford L. McDonald, Lincoln, all of Nebr.; Bennett K. Horenstein, Orinda, Calif.

[73] Assignee: Isco, Inc., Lincoln, Nebr.

[21] Appl. No.: 09/170,535

[22] Filed: Oct. 13, 1998

Related U.S. Application Data

[60] Provisional application No. 60/062,188, Oct. 16, 1997.

[51] Int. Cl.$^6$ .......................... G01N 33/00; G01N 21/00
[52] U.S. Cl. ............................. 436/121; 422/62; 422/81; 422/82; 436/50; 436/52; 436/53; 436/119; 436/177; 436/181; 436/182; 436/183
[58] Field of Search .................................. 422/50, 62, 81, 422/82, 82.01, 82.05; 436/43, 52, 53, 50, 55, 119, 121, 174, 177, 181, 182, 183

[56] References Cited

U.S. PATENT DOCUMENTS

| | | | |
|---|---|---|---|
| 3,705,098 | 12/1972 | Shepherd et al | 210/759 |
| 5,004,696 | 4/1991 | Clinkenbeard | 436/52 X |
| 5,110,744 | 5/1992 | Baughman et al. | 422/62 X |
| 5,218,856 | 6/1993 | Doyle | 73/9.1 |
| 5,356,458 | 10/1994 | Javadi et al. | 436/121 X |
| 5,531,961 | 7/1996 | Wright et al. | 422/80 |

FOREIGN PATENT DOCUMENTS 60-252262 12/1985 Japan .

OTHER PUBLICATIONS

E. J. Keating *Water & Sewage Works* 1978, 125, 68–70.
F. Cadena et al. *J–Water Pollut, Control Fed,* 1988, 60, 1259–1263.

*Primary Examiner*—Arlen Soderquist
*Attorney, Agent, or Firm*—Henderson & Sturm

[57] ABSTRACT

A hydrogen sulfide analyzer that continuously samples waste water from a waste stream or reservoir and measures the concentration of purgeable $H_2S$ present ($H_2SP$) This information, when combined with the volume of water present, provides a control quality signal that regulates the feed rate of the destructor chemical into the waste stream. This results in chemical savings for the user. A second result is the reduction in odor complaints and the corrosion problems associated with $H_2S$ emissions. The analyzer measures only the purgeable $H_2S$ contained in the liquid sample. The analyzer violently agitates the sample containing dissolved $H_2S$ in solution to simulate actual conditions at points of agitation in the waste water stream. It also provides nearly optimal partial pressure conditions for the $H_2S$ to exit the solution as a free gas. Any $H_2S$ that does not come out of solution in the analyzer is not of interest to the user since it will most likely not come out of solution in the treatment process either. The analyzer controls the feed of the destructor chemical based upon the measured quantity and concentration of $H_2S$ that is likely to come out of solution in the collection/treatment process. It does not measure the total amount of sulfides present as other analyzers do. This is an important feature since it is wasteful to treat a condition that is not going to be a problem.

51 Claims, 7 Drawing Sheets

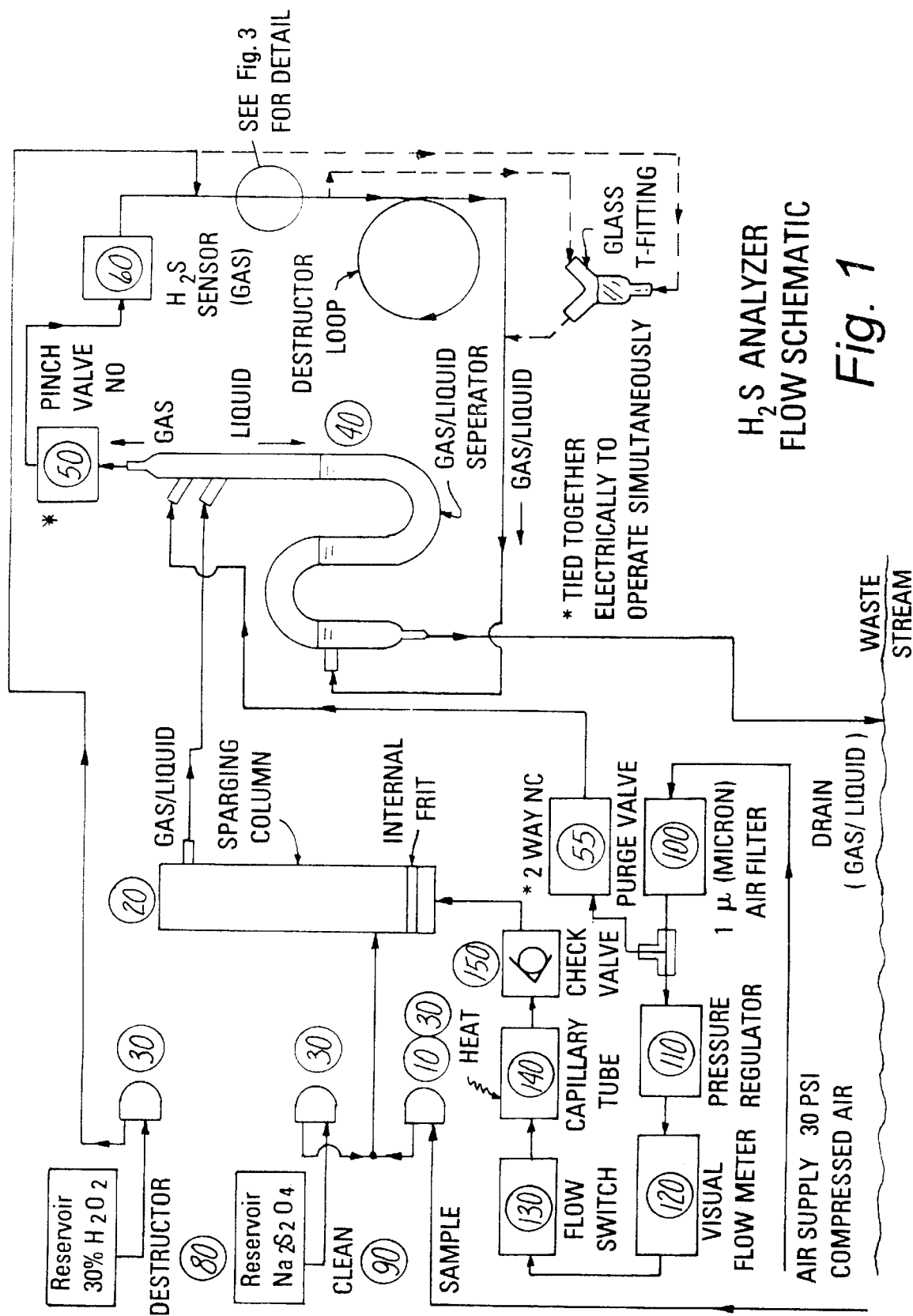

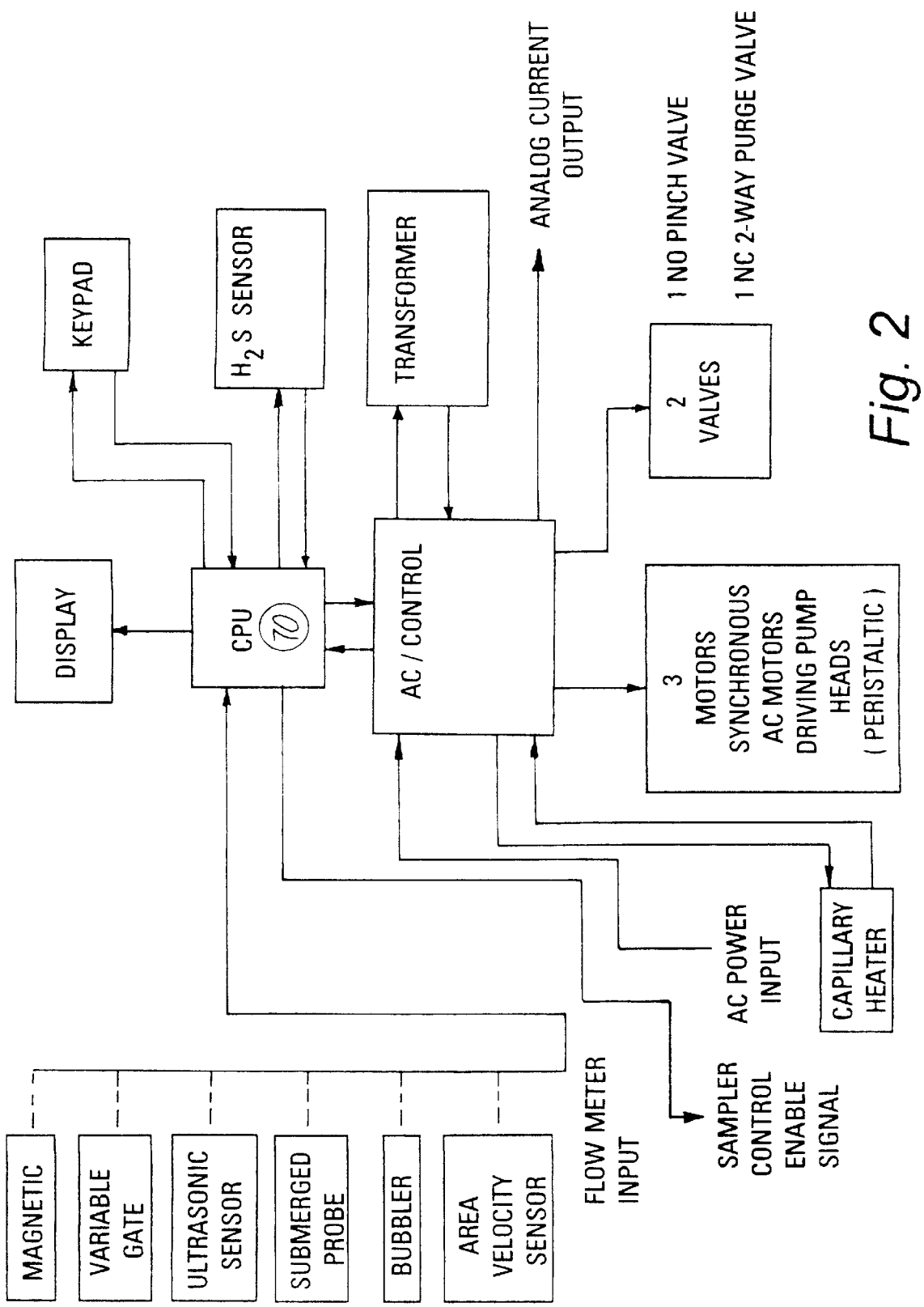

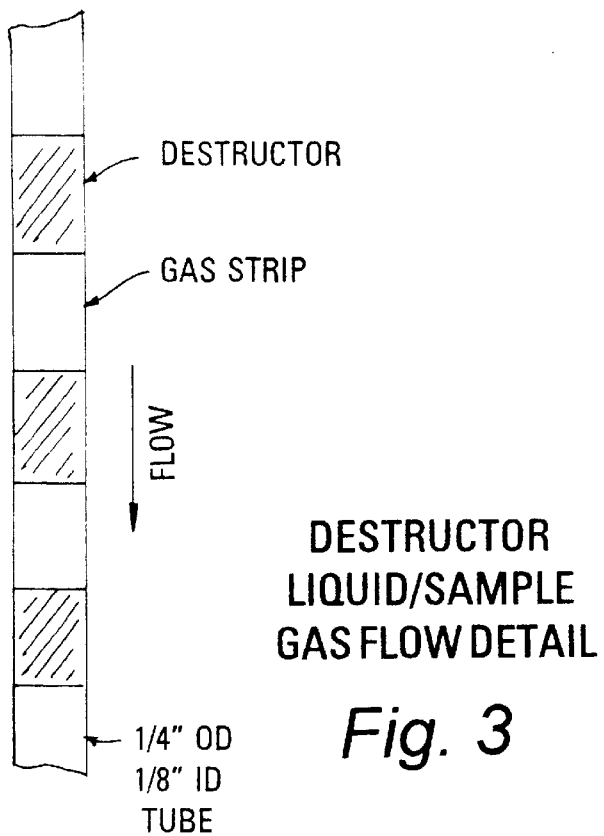
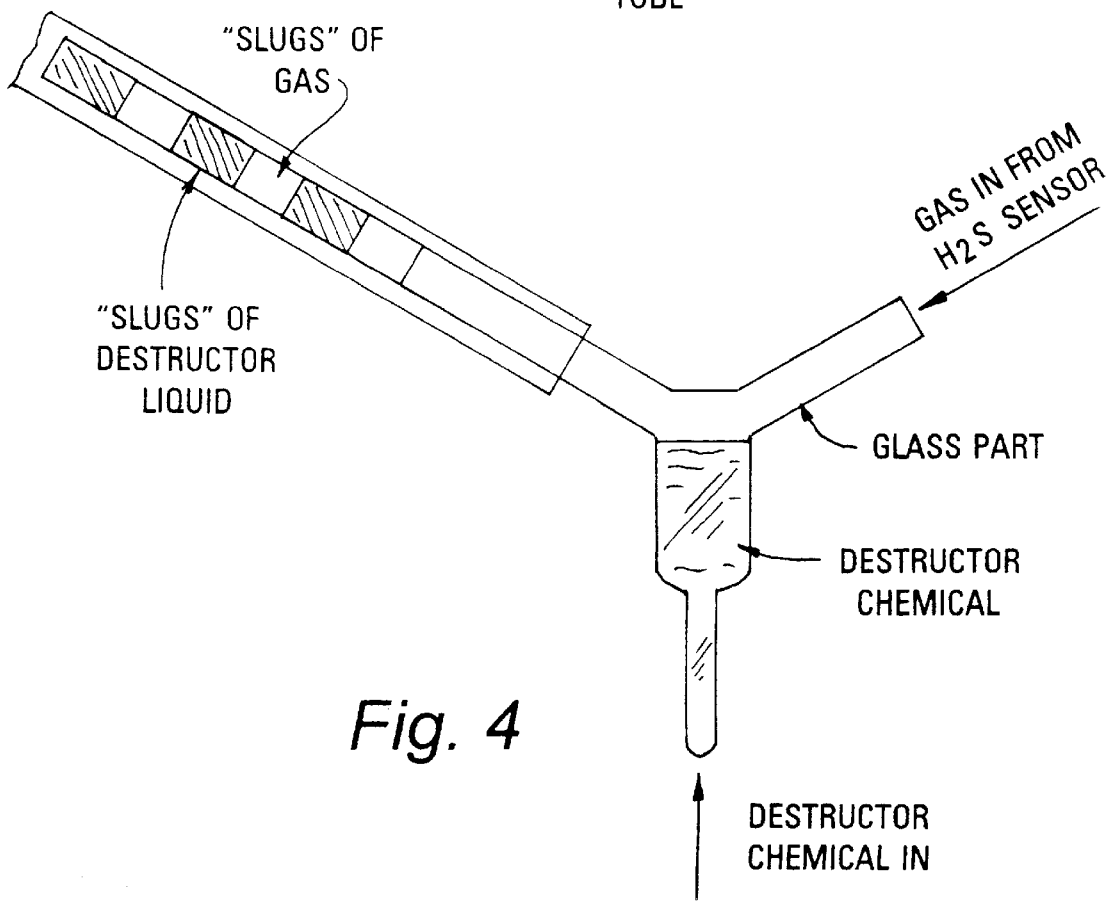

Typical In-Stream Injection System

Typical Air Misting System

HYDROGEN SULFIDE ANALYZER

CROSS REFERENCE TO RELATED APPLICATIONS

This application contains disclosure from and claims the benefit under Title 35 United States Code § 119(e) of United States Provisional Application, Ser. No. 60/062,188, filed Oct. 16, 1997 and entitled "Hydrogen Sulfide Analyzer", which provisional application is incorporated herein by reference.

STATEMENT REGARDING FEDERALLY SPONSORED RESEARCH OR DEVELOPMENT

Not applicable.

REFERENCE TO MICROFICHE APPENDIX

Not applicable.

AUTHORIZATION PURSUANT TO 37 C.F.R. §171 (d) (e)

Not portion of the disclosure of this patent document, including appendices, may contain material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

The present invention relates generally to wet chemical analyzers, and more particularly to an analyzer used for monitoring hydrogen sulfide in waste water.

2. Description of the Related Art

Hydrogen sulfide ($H_2S$) is a gas released as a by-product of biological activity in the collection and treatment of waste water. $H_2S$ is extremely corrosive to equipment and poisonous to the human body. In addition, the majority of odor complaints incurred by waste treatment operations can be traced to fugitive emissions of $H_2S$.

$H_2S$ gas is soluble in water. However, if water containing dissolved $H_2S$ is agitated, the $H_2S$ tends to come out of solution as a gas. This gas is corrosive and poisonous. Several control strategies are employed in the industry to control the emission of $H_2S$ gas. It is common practice to mount free air $H_2S$ detectors just above flowing streams of waste water at points of agitation. These include weirs, flumes, inverts, pump stations, etc. These free air sensors detect the $H_2S$ only after it is released into the air. Because they are affected by air currents, they do not give any reliable data about the concentration of $H_2S$ in the stream being monitored. Essentially these devices become air quality violation yes/no indicators. They indicate either that there is a violation or that there is no violation. The most efficient way to control $H_2S$ is to convert it into inert compounds while it is still dissolved in the waste water. In this state, there are many well known control strategies for converting $H_2S$ into inert compounds.

To control $H_2S$ that is dissolved into waste water, various chemicals are fed into the waste water that convert $H_2S$ into non-toxic and non-destructive compounds. These chemicals are fed into the waste water based upon the volume of water to be treated. However, $H_2S$ may or may not be present in the waste water at all times or in consistent concentrations. This results in too little or too much destructor chemical being injected into the waste water the majority of the time. When too little destructor chemical is fed, only a portion of the $H_2S$ will be destroyed. When too much destructor chemical is fed, the user is paying for chemicals that are being wasted. Once injected, most destructor chemicals are active for approximately 15 minutes or until consumed, whichever comes first.

Those concerned with these and other problems recognize the need for an improved hydrogen sulfide analyzer.

BRIEF SUMMARY OF THE INVENTION

The present invention discloses a hydrogen sulfide analyzer that continuously samples waste water from a waste stream or reservoir and measures the concentration of purgeable $H_2S$ present ($H_2SP$). This information, when combined with the volume of water present, provides a control quality signal that regulates the feed rate of the destructor chemical into the waste stream. This results in chemical savings for the user. A second result is the reduction in odor complaints and the corrosion problems associated with $H_2S$ emissions. The analyzer measures only the purgeable $H_2S$ contained in the liquid sample. The analyzer violently agitates the sample containing dissolved $H_2S$ in solution to simulate actual conditions at points of agitation in the waste water stream. It also provides nearly optimal partial pressure conditions for the $H_2S$ to exit the solution as a free gas. Any $H_2S$ that does not come out of solution in the analyzer is not of interest to the user since it will most likely not come out of solution in the treatment process either. The analyzer controls the feed of the destructor chemical based upon the measured quantity and concentration of $H_2S$ that is likely to come out of solution in the collection/treatment process. It does not measure the total amount of sulfides present as other analyzers do. This is an important feature since it is wastefull to treat a condition that is not going to be a problem.

An object of the present invention is to provide an analyzer that measures the purgeable $H_2S$ in the liquid substrate.

A further object of the present invention is to provide a $H_2S$ analyzer that creates control quality signals that can control the dispensing of destructor chemicals.

A still further object of the present invention is to provide a $H_2S$ analyzer that controls the injection of destructor chemicals if, when, and in the proper amount based upon need.

Another object of the present invention is to provide an analyzer that provides a measurement of $H_2S$ concentration levels.

Yet another object of the present invention is to provide a $H_2S$ analyzer that can be located close to the stream.

Still another object of the present invention is to provide an analyzer wherein the sample temperature is maintained at ambient conditions or controlled prior to analysis, since temperature affects $H_2S$ volatility.

A further object of the present invention is to provide an analyzer that measures purgeable $H_2S$ at the current ambient sample conditions.

A still further object of the present invention is to provide a $H_2S$ analyzer that is self cleaning.

Another object of the present invention is to provide a $H_2S$ analyzer that combines and accounts for the liquid flow rate of the stream when creating control signals for the destructor chemical dispensing equipment.

Yet another object of the present invention is to provide an analyzer that prevents releasing H$_2$S gas as a by-product of the analysis.

Still another object of the present invention is to provide a H$_2$S analyzer with the ability to trigger the activation of a sampler to take samples when an alarm condition is detected.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 1 is flow schematic of the hydrogen sulfide analyzer of the present invention;

FIG. 2 is a schematic illustrating the inputs to and outputs from the analyzer on-board microprocessor;

FIG. 3 is a schematic illustrating the gas/fluid flow in the destructor loops that prevent the release of H$_2$S from the analyzer;

FIG. 4 is a schematic illustrating the gas/fluid flow in the glass fitting that is an alternative to the destructor loops;

DETAILED DESCRIPTION OF THE INVENTION

Figure 5:
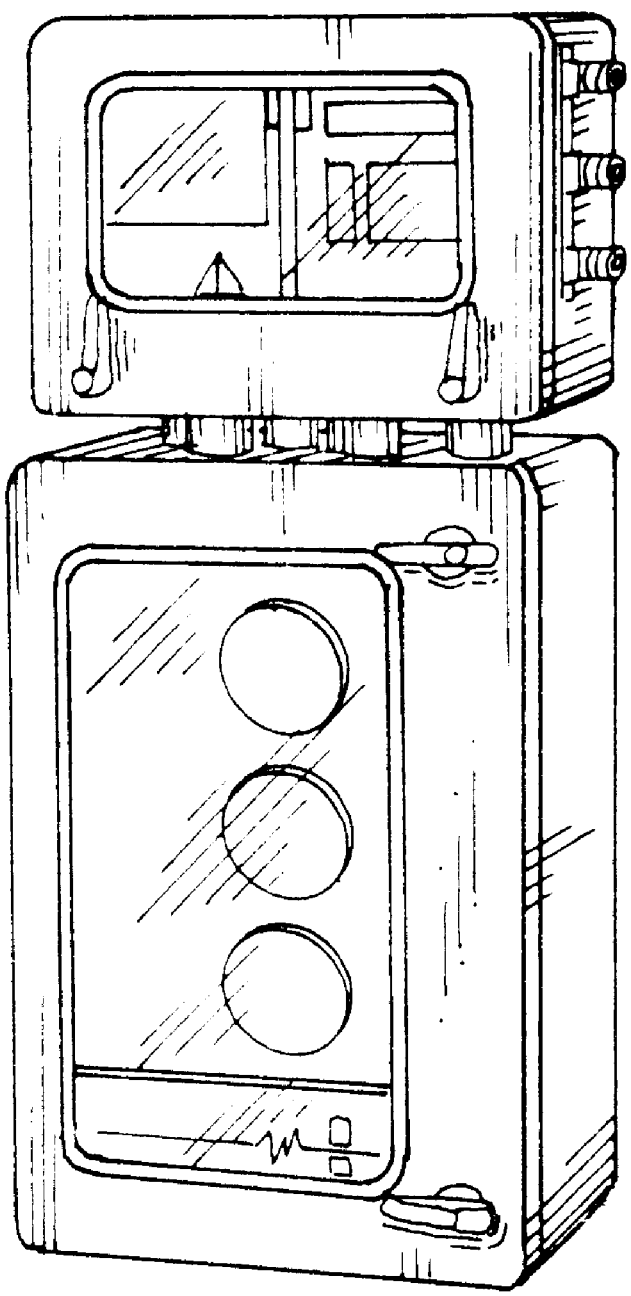
FIG. 5 is a perspective view of the analyzer showing the two-cabinet design.

As can be seen by reference to the drawings, FIG. 1 shows a flow schematic of the hydrogen sulfide analyzer 1 of the present invention. The analyzer operation is based upon the volatile nature of H$_2$S. H$_2$S gas is soluble in water. When water containing H$_2$S is agitated, the H$_2$S comes out of solution.

The analyzer 1 continuously draws a sample stream from the waste water source to be analyzed. The sample is drawn into the analyzer 1 from the source by a peristaltic pump 10. This stream is then injected into the sparging column 20. The sparging column 20 is also fed by a stream of compressed gas to be described later. The waste water is agitated by the flow of the gas stream as it flows upwards through the sparging column 20 due to buoyancy. The gas stream simultaneously provides a partial pressure situation that strips the H$_2$S out of solution and carries it away. The volumetric flow of the gas stream is regulated for consistency. The volumetric flow of waste water being analyzed is also regulated for consistency. The waste water flow is regulated via the peristaltic pump 10 being driven by a synchronous constant speed AC gear motor 30.

At the exit of the sparging column, there exists the original waste water, the H$_2$S gas that was stripped from the waste water, and the carrier gas that provided the agitation and sparging. The mixed stream of gasses and liquids are fed into a gas/liquid separator (GLS) 40.

It is to be understood that alternate methods of purging the H$_2$S from the sample could be used to simulate the conditions at points of agitation in the waste water stream. Mechanical mixing could be provided by the agitation of a spinning device submerged or partially submerged in the sample to effectively drive the H$_2$S and any other volatiles from the sample solution. Acoustic agitation using a frequency coupled mechanical device such as piezo film or a basic submerged speaker could be used to impart wave energy to the sample. If the frequency of the wave energy was matched with the fundamental oscillation frequency of the H$_2$S molecule, effective volatilization of the H$_2$S would result. Vibration of the sample liquid containing H$_2$S could be accomplished mechanically. As indicated above, matching the vibration frequency and amplitude to the molecular structure would optimize results. Sparging by heating the sample liquid would also cause the H$_2$S to come out of solution. There would be a specific temperature at which all of the H$_2$S would exit the solution. Heating past this temperature would have no further benefit. This would be similar to a distillation process where specific weight volatiles come off at specific temperatures. Also, chemical stripping could be done by the addition of a weak acid, and possibly other chemicals, to drive the H$_2$S from solution by reducing the solubility of H$_2$S in the sample substrate.

The liquid emanating from the GLS 40 is routed to drain through a standard P-trap arrangement. Any solids that entered the analyzer 1 in the sample substrate will be collected in the lowest portion of the P-trap. The liquid portion of the substrate over flows the P-trap and is routed back to the sample source via a gravity drain. To remove the accumulated solids from the P-trap, a pinch valve 50 and a purge valve 55 are utilized on the gas exit of the P-trap. The pinch valve 50 is a two way normally open valve. The purge valve 55 is a 2-way normally closed valve located between the air supply and the P-trap. The valves 50 and 55 are energized at time intervals entered into the program by the user. When the valves 50 and 55 are energized the flow of gas from the P-trap is blocked. This results in the gas stream being forced through the liquid portion of the P-trap. The purge valve 55 also opens and injects 30 psi air into the top of the P-trap. The action of this gas flow exiting through the P-trap at high velocity flushes out any solids that accumulate in the base of the trap and routes them to the drain. The interval between these flush events is selected based upon the rate of solids accumulation in the trap. This time interval will vary depending upon the sample conditions.

The gas stream exits from the GLS 40 and passes through the pinch valve 50 descried above. This gas stream contains the carrier gas and any H$_2$S that was purged from the sample. From this point the gas stream is routed to the H$_2$S sensor 60 where the concentration of H$_2$S in the gas stream is measured. The H$_2$S concentration data from the sensor is monitored by the on-board microprocessor 70. (See FIG.2).

By knowing the amount of sample being fed into the analysis, the amount of sparge gas being fed into the sample, and the final concentration of H$_2$S in this gas stream, the processor 70 is able to determine the amount of purgeable H$_2$S that is present in the sample being analyzed. This data, when scaled with flow data, provides a control quality 4–20 mA signal that is used to control the treatment of purgeable H$_2$S in the waste water. In this preferred embodiment, the signal controls the feed rate of destructor chemical to eliminate the purgeable H$_2$S.

It is to be understood that effective treatment of the H$_2$S in the waste water may be accomplished by means other than the addition of destructor chemicals such as hydrogen peroxide or chlorine. Other effective treatments of the $H_2S$ include activation or deactivation of liquid-gas scrubbers; addition of biological substances; adjustment of the pH; adjustment of dissolved oxygen levels; and other treatments currently known or that may be later developed.

After passing through the $H_2S$ sensor 60, destructor chemical is fed into the gas stream within the analyzer 1. Due to the pulsing nature of the peristaltic destructor chemical pump 80 and the nature of gas flow in circular conduit, the resulting gas liquid stream is comprised of volumes of gas separated by volumes of destructor liquid. See FIG. 3, showing the destructor liquid/sample gas flow detail. The conduit carrying this mixture is formed into a number of destructor loops to provide enough contact time for the destructor chemical to convert the $H_2S$ present in the gas stream into inert compounds. A typical destructor liquid is hydrogen peroxide or chlorine. However, there are many compounds known to chemically convert $H_2S$ into inert compounds. The number of destructor loops can be varied depending upon the concentration of $H_2S$ in the gas stream and the effectiveness of the chosen destructor liquid. The analyzer 1 illustrated in FIG. 1 contains one loop, but the number of loops may be increased if needed to prevent any emission of $H_2S$ by the analyzer 1.

An alternative method of achieving the injection of destructor chemical into the analysis gas stream is to use a glass fitting in place of the destructor loop. Referring to FIG. 4, the destructor chemical is fed into the bottom of the glass fitting that is essentially an enlarged T-fitting. The gas stream containing the $H_2S$ flows into the top of the fitting. The contact of the gas to the free surface of the destructor chemical will begin the conversion of the $H_2S$ into inert compounds. This conversion will continue as the gas/liquid mixture flows in an interrupted pattern in the conduit away from the glass fitting.

After passing through the destructor loop or destructor glassware, the gas liquid mixture is routed to the drain of the GLS 40. Here it combines with the liquid portion of the original sample as it falls by gravity drain back to the sample source.

At intervals programmed by the user, the analyzer 1 will clean the sparging column 20. Under control of the on board microprocessor 70, the sample pump 10 is stopped and the clean pump 90 is started simultaneously. The clean pump 90 is of the same type and drive as the other two peristaltic pumps 10 and 80 described earlier. When this occurs, a cleaning solution, typically 1.5 molar sodium persulfate solution in water, is pumped into the sparging column 20 instead of the sample. The oxidizing nature of the cleaning solution will remove accumulated debris from the interior of the sparging column 20 and route them to the GLS 40. Some cleaning of the GLS 40 by the solution will also be accomplished. The interval and duration of the cleaning cycle is programmed by the user. The duration and interval are adjusted based upon sample conditions. The cleaning cycle can also be manually initiated by the user.

The final system on the flow schematic of FIG. 1 is the air supply. The compressed atmospheric air enters the analyzer 1 at 30 psi. The compressed air can be supplied via bottles or via an air compressor. After entry into the analyzer 1 the compressed air is routed to the air filter 100. The air filter 100 removes any particles that may be contained in the air stream that are larger than 1 micron. From the air filter 100, the compressed air is routed through a T-fitting to both the pressure regulator 110 and the inlet of the purge valve 55. The purge valve 55 is used in cleaning the analyzer 1. The function of this component is described elsewhere. The pressure regulator 110 controls the input pressure to the capillary tube (described later). The pressure regulator 110 and the capillary tube work together to adjust and maintain the proper air flow into the sparging column 20. From the pressure regulator 110 the compressed air passes through the visual flow meter 120. The visual flow meter 120 is a device that gives the operator a visual display of the current flow rate of compressed air through the analyzer 1. Next, the compressed air supply passes through the flow switch 130. The flow switch 130 is a device that provides a contact closure any time that the air flow through the switch 130 drops below 25 cc/min. If the airflow through the switch 130 falls below 25 cc/min, it is assumed that the compressed air supply to the analyzer 1 has failed. The microprocessor 70 monitors the switch 130 and signals the operator if a failure in the air supply is detected. From the flow switch 130, the compressed air supply next passes through the capillary tube 140. The capillary tube 140 is a 1 meter long tube wrapped around a cylindrical heater. Under control of the microprocessor 70 and a temperature sensor, the heater maintains the capillary tube at 60 degrees C. The capillary tube is a pipe with an inside diameter of 0.020 inches. This small passage creates a large pressure differential in the compressed air supply between the inlet and the outlet of the capillary tube. By regulating the pressure into the capillary tube and maintaining a constant temperature of the tube, the flow rate through the tube becomes proportional to the input pressure. This is important since this air stream is used for both sparging and carrying the purged $H_2S$ through the sensor 60. The air flow must remain constant to preserve the proper dilution ratio of $H_2S$ flowing past the sensor 60. The final component in the air supply is the check valve 150. The check valve 150 prevents liquid from entering the air system components if the compressed air supply to the analyzer 1 fails.

FIG. 5 shows a two-cabinet design that physically separates the electronics in the upper cabinet from the chemical and hydraulic components in the lower cabinet. The analyzer 1 is designed to operate in harsh conditions with a NEMA 4X (IP65) enclosure for protection against corrosive atmospheres.

Figure 6:
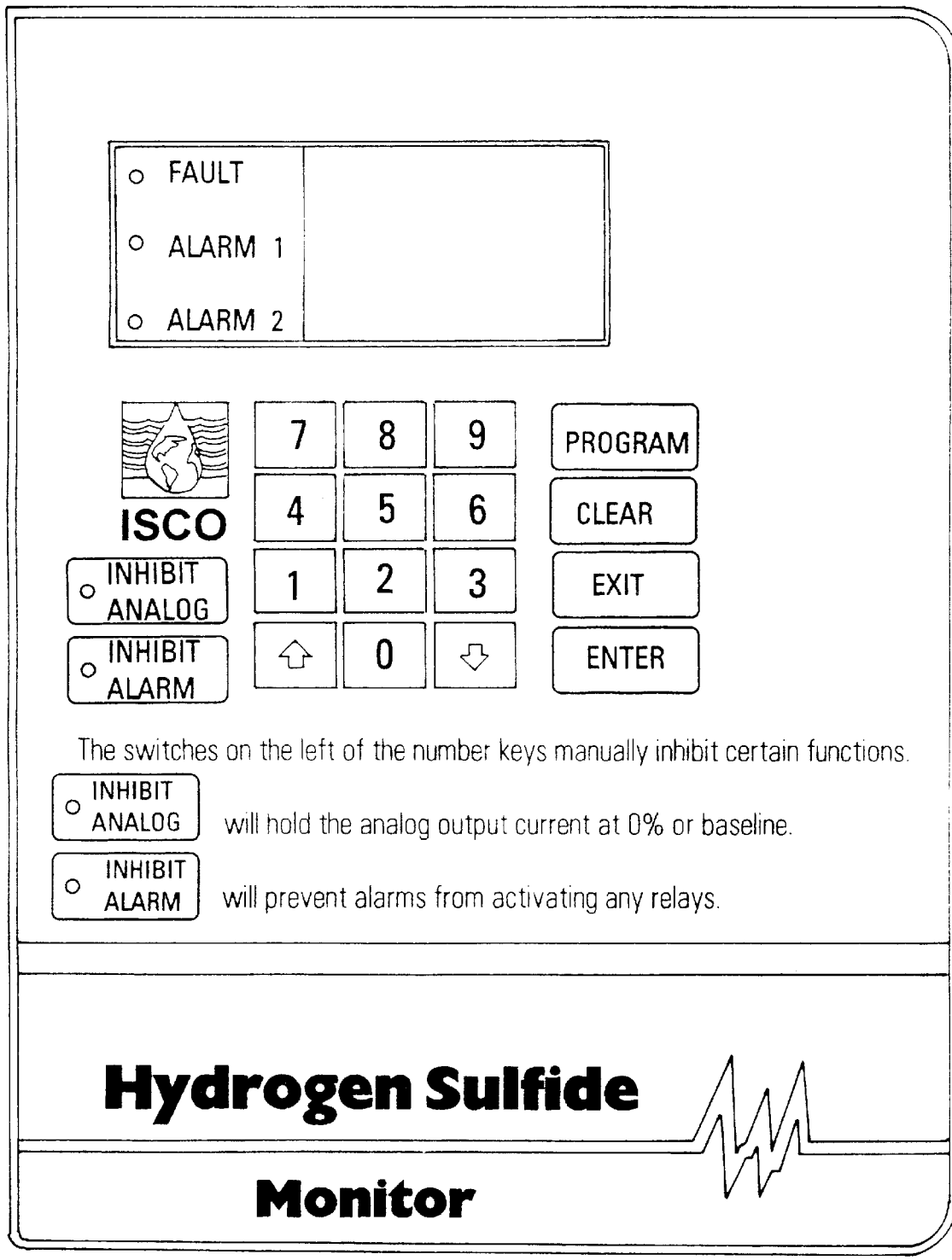
FIG. 6 is an enlarged front elevational view illustrating the keypad and display.

Referring now to the CPU flow chart of FIG. 2, it can be seen that all inputs/outputs flow through the CPU unit 70. The display and keypad are shown in FIG. 6. They are self-explanatory and form the user interface for input/retrieval of information.

The $H_2S$ sensor 60 is a solid state semiconductor $H_2S$ sensor part #3999 supplied by Detcon, Inc., The Woodlands, Tex. 77387. The electrical signal that is proportional to $H_2S$ is communicated to the CPU 70. The AC controller handles all AC power distribution in the unit.

Also communicating with the CPU 70 is the flow meter input and analog current output. The CPU 70 uses both the concentration of $H_2S$ being detected in the analyzer 1 and the current flow rate of the waste water to create the analog current output. The analog current output is then used by the destructor chemical feed apparatus to set the rate of chemical feed, or the analog current output is used to control the purgeable $H_2S$ in the waste stream by other means as discussed above. The analog current output is a 4–20 mA current loop. The flow data is used as a scalar for the detected $H_2S$ concentration to set the current output level. This means that 4 mA=0 purgeable $H_2S$ units. 20 mA=fall scale flow and full scale purgeable $H_2S$ units. Between these two points, the output varies linearly with flow and $H_2S$ concentration. It is understood that the system will also operate without flow meter input. In this embodiment, the output signal will vary based upon purgeable H₂S only.

Figure 7:
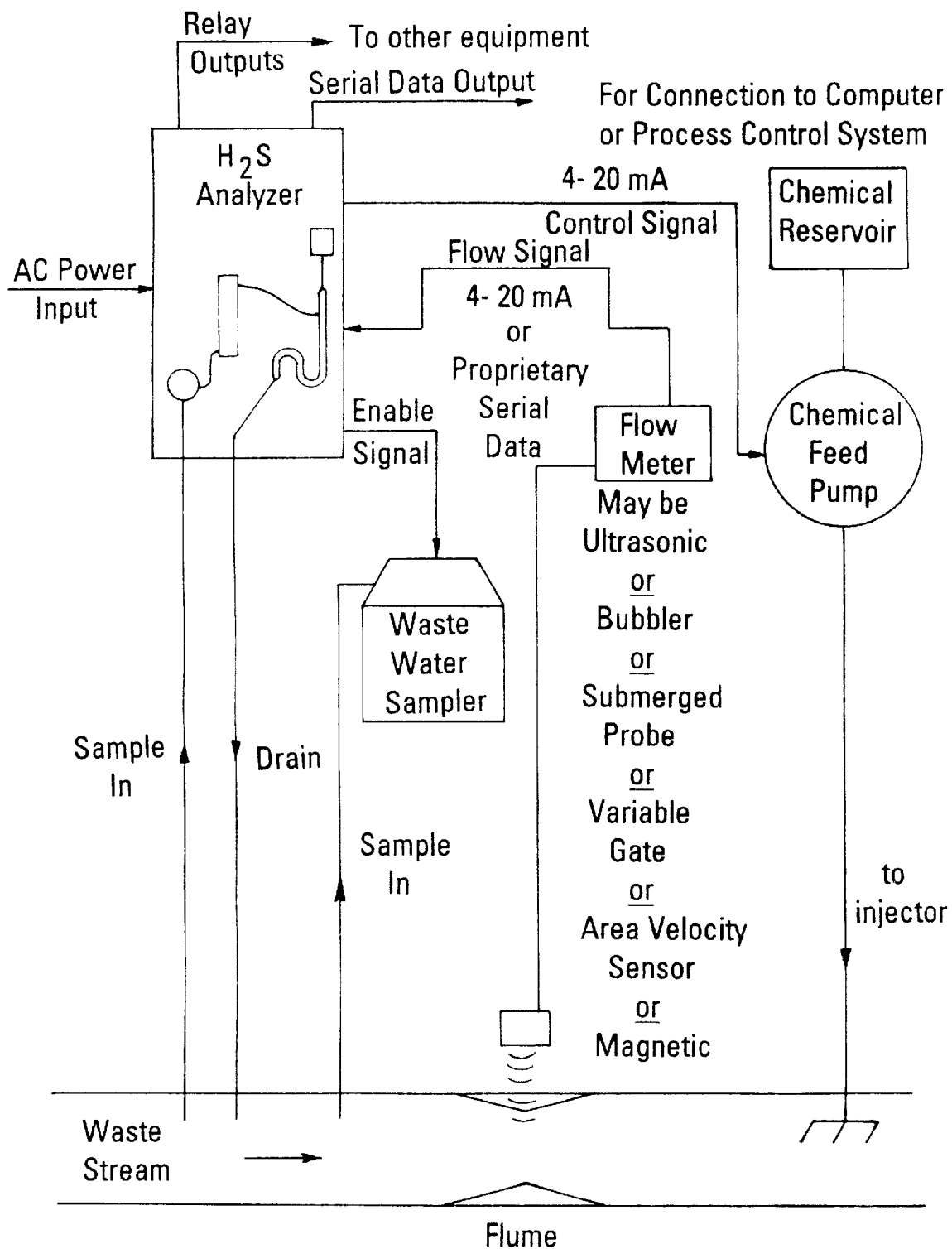
FIG. 7 is a schematic of the analyzer of the present invention integrated with an alarm triggered automatic sampler.
Figure 8:
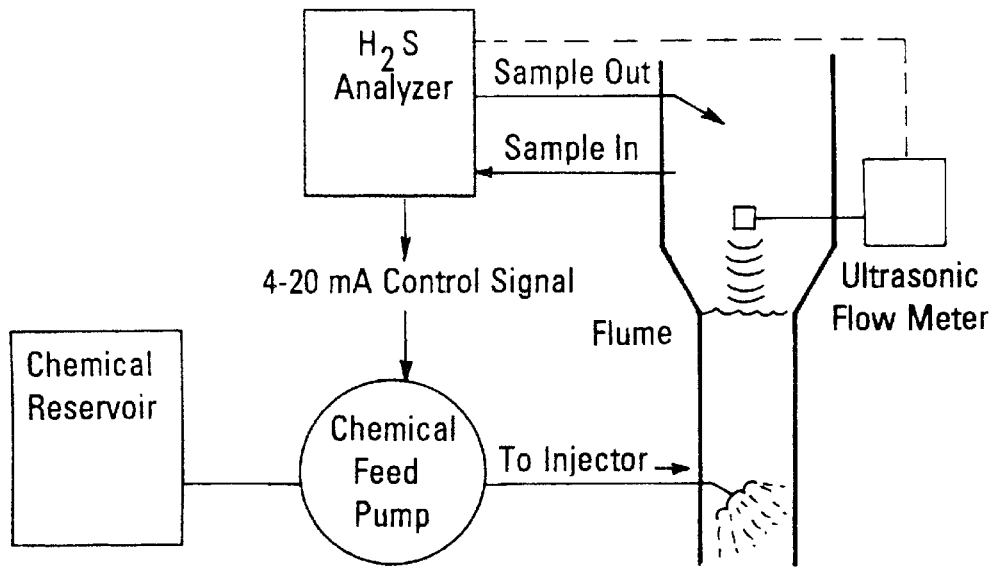
FIG. 8 is a schematic illustrating a typical in-stream injection system.
Figure 9:
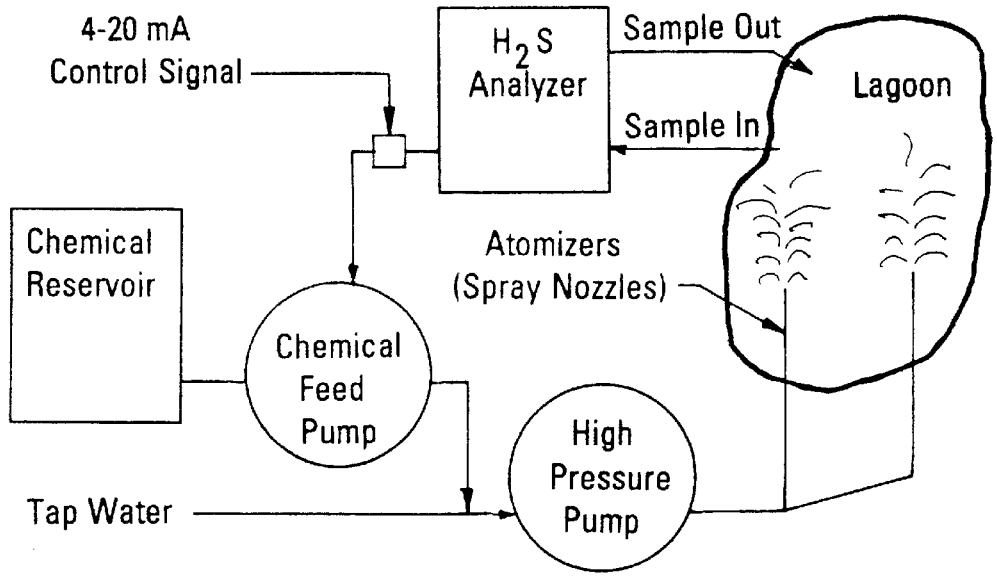
FIG. 9 is a schematic illustrating a typical air misting system.

FIG. 7 shows the analyzer 1 integrated with an alarm triggered automatic sampler. FIGS. 8 and 9 illustrate typical in-stream injection and air misting systems, respectively. The waste water sampler depicted in FIG. 7 could be one of several models supplied by ISCO, Inc. of Lincoln, Neb. or other suppliers. The flow meter depicted in FIGS. 7 and 8 is an ultrasonic sensor; however, it is to be understood that other types of flow meters including submerged probe, bubbler, variable gate, area velocity sensors, and magnetic sensors supplied by ISCO, Inc. or others could be used.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

In the claims, means-plus-function clauses are intended to cover the structures described herein as performing the recited function and not only structural equivalents, but also equivalent structures.

We claim:

1. A hydrogen sulfide analyzer, consisting essentially of:
   means for sampling waste water from a waste stream to obtain a sample;
   means for purging hydrogen sulfide from the sample to simulate actual conditions of agitation in the waste stream and to release purgeable hydrogen sulfide from the sample wherein the purging means is a sparging column having a sample inlet port disposed to receive the sample, a sparging gas inlet port disposed to receive a substantially neutral gas, and an outlet port;
   means for measuring the concentration of purgeable hydrogen sulfide purged from the sample disposed in communication with the outlet port of the sparging column; and
   means for treating the waste stream based upon the measured purgeable hydrogen sulfide concentration.

2. The analyzer of claim 1 wherein the neutral gas is air supplied via an air compressor.

3. The analyzer of claim 1 wherein the neutral gas is air supplied via pressurized supply bottles.

4. The analyzer of claim 1 wherein the neutral gas is supplied to the sparging column inlet port at a flow rate greater than about 10 cc per minute.

5. The analyzer of claim 4 wherein the neutral gas is supplied through a capillary that is maintained at about 60° C.

6. The analyzer of claim 5 wherein the flow rate is proportional to a predetermined pressure.

7. The analyzer of claim 6 wherein the inlet pressure is maintained in a range of about 10–150 psi.

8. The analyzer of claim 1 further including means for measuring the flow rate of the waste stream.

9. The analyzer of claim 8 wherein the flow rate measuring means is a bubbler flow meter.

10. The analyzer of claim 8 wherein the flow rate measuring means is an ultrasonic flow meter.

11. The analyzer of claim 8 wherein the flow rate measuring means is a submerged probe flow meter.

12. The analyzer of claim 8 wherein the flow rate measuring means is a variable gate flow meter.

13. The analyzer of claim 8 wherein the flow rate measuring means is an area velocity flow meter.

14. The analyzer of claim 1 wherein the waste stream treating means includes the addition of destructor chemical into the waste stream at a rate based upon the measured purgeable hydrogen sulfide concentration.

15. The analyzer of claim 14 further including means for measuring the flow rate of the waste stream.

16. The analyzer of claim 15 further including means for controlling the destructor chemical adding means based on the measured purgeable hydrogen sulfide concentration and the measured waste stream flow rate.

17. The analyzer of claim 16 wherein the controlling means includes a microprocessor.

18. The analyzer of claim 17 wherein inputs to the microprocessor include a signal from the purgeable hydrogen sulfide concentration measuring means and a signal from the waste stream flow rate measuring means.

19. The analyzer of claim 18 wherein outputs from the microprocessor include an analog current output to the destructor chemical adding means.

20. The analyzer of claim 1 wherein the waste stream treating means includes the adjustment of the pH of the waste stream.

21. A method of controlling hydrogen sulfide odor in a waste stream, comprising the steps of:
   sampling waste water from a waste stream to obtain a sample;
   purging hydrogen sulfide from the sample to simulate actual conditions of agitation in the waste stream and to release purgeable hydrogen sulfide from the sample;
   measuring the concentration of purgeable hydrogen sulfide purged from the sample; and
   treating the waste stream based upon the measured purgeable hydrogen sulfide concentration.

22. The method of claim 21, wherein the purging step is done in a sparging column using a substantially neutral gas.

23. The method of claim 22 wherein the sparging column includes a sample inlet port, a sparging gas inlet port, and outlet port: and wherein the neutral gas is pressurized and disposed in communication with the sparging gas inlet port.

24. The method of claim 23 wherein the neutral gas is atmospheric air supplied via an air compressor.

25. The method of claim 23 wherein the neutral gas is atmospheric air supplied via pressurized supply bottles.

26. The method of claim 23 wherein the neutral gas is supplied to the sparging column inlet port at a flow rate greater than about 10 cc per minute.

27. The method of claim 26 wherein the neutral gas is supplied through a capillary that is maintained at about 60° C.

28. The method of claim 27 wherein the flow rate is proportional to a predetermined pressure.

29. The method of claim 28 wherein the inlet pressure is maintained in a range of about 10–150 psi.

30. The method of claim 21 wherein the purging step includes mechanical mixing of the sample.

31. The method of claim 21 wherein the purging step includes acoustic agitation of the sample.

32. The method of claim 21 wherein the purging step includes mechanical vibration of the sample.

33. The method of claim 21 wherein the purging step includes heating of the sample.

34. The method of claim 21 further including the step of for measuring the flow rate of the waste stream.

35. The method of claim 34 wherein the flow rate is measured by a bubbler flow meter.

36. The method of claim 34 wherein the flow rate is measured by an ultrasonic flow meter.

37. The method of claim 34 wherein the flow rate is measured by a submerged probe flow meter.

38. The method of claim 34 wherein the flow rate is measured by a variable gate flow meter.

39. The method of claim 34 wherein the flow rate is measured by an area velocity flow meter.

40. The method of claim 21 wherein the treatment of the wastestream includes the addition of destructor chemical into the waste stream at a rate based upon the measured purgeable hydrogen sulfide concentration.

41. The method of claim 40 further including means for measuring the flow rate of the waste stream.

42. The method of claim 41 further including the step of controlling the destructor chemical addition based on the measured purgeable hydrogen sulfide concentration and the measured waste stream flow rate.

43. The method of claim 42 wherein the controlling means includes a microprocessor.

44. The method of claim 43 wherein inputs to the microprocessor include a signal corresponding to the measured purgeable hydrogen sulfide concentration and a signal corresponding to the measured waste stream flow rate.

45. The method of claim 44 wherein outputs from the microprocessor include an analog current output to control the addition of destructor chemical.

46. The method of claim 21 wherein the waste stream is treated by the adjustment of the pH of the waste stream.

47. A hydrogen sulfide analyzer, consisting essentially of:
a sampler disposed to receive a liquid sample from a waste system;
a sparging column including an inlet port disposed to receive the liquid sample, a sparging gas inlet port disposed to receive a substantially neutral gas, and an outlet port for discharging liquid and gas fractions generated by agitation of the liquid sample by the neutral gas, the sparging column acting to simulate actual conditions of agitation in the waste stream and to release purgeable hydrogen sulfide from the liquid fraction into the gas fraction;
a hydrogen sulfide detector disposed to receive the gas fraction from the outlet port of the sparging column and measure the purgeable hydrogen sulfide concentration of the gas fraction; and
an injector disposed to deliver a destructor chemical into the waste stream at a rate based upon the measured purgeable hydrogen sulfide concentration.

48. A volatile gas analyzer, consisting essentially of:
a sampler disposed to receive a liquid sample from a stream;
a sparging column including an inlet port disposed to receive the liquid sample, a sparging gas inlet port disposed to receive a substantially neutral gas, and an outlet port for discharging liquid and gas fractions generated by agitation of the liquid sample by the neutral gas, the sparging column acting to simulate actual conditions of agitation in the stream and to release a specific purgeable gas from the liquid fraction into the gas fraction;
a gas detector disposed to receive the gas fraction from the outlet port of the sparging column and measure the concentration of the specific purgeable gas contained in the gas fraction; and
an injector disposed to deliver a destructor chemical into the stream at a rate based upon the measured concentration of the specific purgeable gas.

49. The analyzer of claim 48 wherein the specific purgeable gas is hydrogen sulfide.

50. The analyzer of claim 49 wherein the destructor chemical is hydrogen peroxide.

51. The analyzer of claim 49 wherein the destructor chemical is chlorine.

* * * * *